US006582704B2

(12) United States Patent
Urban et al.

(10) Patent No.: US 6,582,704 B2
(45) Date of Patent: Jun. 24, 2003

(54) IMMUNOGENIC PEPTIDES FROM THE HPV E7 PROTEIN

(75) Inventors: Robert G. Urban, Lexington, MA (US); Roman M. Chicz, Belmont, MA (US); Edward J. Collins, Carrboro, NC (US); Mary Lynne Hedley, Lexington, MA (US)

(73) Assignee: Zycos Inc., Lexington, MA (US)

( * ) Notice: Subject to any disclaimer, the term of this patent is extended or adjusted under 35 U.S.C. 154(b) by 0 days.

(21) Appl. No.: 09/759,960

(22) Filed: Jan. 12, 2001

(65) Prior Publication Data

US 2001/0006639 A1 Jul. 5, 2001

Related U.S. Application Data

(62) Division of application No. 09/169,425, filed on Oct. 9, 1998, now Pat. No. 6,183,746.
(60) Provisional application No. 60/061,657, filed on Oct. 9, 1997.

(51) Int. Cl.[7] .................. A61K 39/12; A61K 38/00; C07H 21/04
(52) U.S. Cl. ............... 424/204.1; 424/186.1; 424/185.1; 435/69.1; 435/69.7; 536/23.72; 530/300; 530/350
(58) Field of Search .......... 424/204.1, 186.1, 424/185.1; 536/23.72; 530/300, 350; 435/69.7, 69.1; 930/220

(56) References Cited

U.S. PATENT DOCUMENTS

| | | | |
|---|---|---|---|
| 4,741,872 A | 5/1988 | DeLuca et al. | 264/4.7 |
| 4,777,239 A | 10/1988 | Schoolnik et al. | 530/326 |
| 5,075,109 A | 12/1991 | Tice et al. | 424/88 |
| 5,413,797 A | 5/1995 | Khan et al. | 424/489 |
| 5,547,846 A | 8/1996 | Bartsch et al. | 435/7.1 |
| 5,580,859 A | 12/1996 | Felgner et al. | 514/44 |
| 5,589,466 A | 12/1996 | Felgner et al. | 514/44 |
| 5,593,972 A | 1/1997 | Weiner et al. | 514/44 |
| 5,643,605 A | 7/1997 | Cleland et al. | 424/489 |
| 5,648,459 A | 7/1997 | Cole et al. | 530/324 |
| 5,656,297 A | 8/1997 | Bernstein et al. | 424/484 |
| 5,679,647 A | 10/1997 | Carson et al. | 514/44 |
| 5,695,770 A | 12/1997 | Raychaudhuri et al. | 424/278.1 |
| 5,703,055 A | 12/1997 | Felgner et al. | 514/44 |
| 5,705,151 A | 1/1998 | Dow et al. | 424/93.21 |
| 5,709,860 A | 1/1998 | Raychaudhuri et al. | 424/184.1 |
| 5,733,548 A | 3/1998 | Restifo et al. | 424/184.1 |
| 5,783,567 A | 7/1998 | Hedley et al. | 514/44 |
| 5,846,540 A | 12/1998 | Restifo et al. | 424/192.1 |
| 6,007,806 A | 12/1999 | Lathe et al. | 424/93.2 |
| 6,013,258 A | 1/2000 | Urban et al. | 424/186.1 |
| 6,037,135 A | 3/2000 | Kubo et al. | 435/7.24 |

FOREIGN PATENT DOCUMENTS

| | | | |
|---|---|---|---|
| JP | 60-147368 | | 7/1985 |
| WO | WO92/10513 | * | 6/1992 |
| WO | WO 93/22338 | | 11/1993 |
| WO | WO 94/03205 | | 2/1994 |
| WO | WO94/04171 | * | 3/1994 |
| WO | WO 94/04557 | | 3/1994 |
| WO | WO 94/20127 | | 9/1994 |
| WO | WO 94/21680 | | 9/1994 |
| WO | WO 94/23738 | | 10/1994 |
| WO | WO 95/24929 | | 11/1995 |
| WO | WO 96/00583 | | 1/1996 |
| WO | WO 97/17063 | | 5/1997 |
| WO | WO 97/33602 | | 9/1997 |
| WO | WO 97/34617 | | 9/1997 |
| WO | WO 97/34621 | | 9/1997 |
| WO | WO 97/42940 | | 11/1997 |
| WO | WO 98/31398 | | 7/1998 |
| WO | WO 99/45954 | | 9/1999 |

OTHER PUBLICATIONS

Collins et al., "processing of Exogenous Lipsome–Encapsulat4ed Antigens In Vivo Generates Class I MHC–restricted T Cell Responses," The Journal of Immunology, 148:3336–3341, No. 11, Jun. 1, 1992.

Elliott et al., "Processing of Major Histocompatibility Class I–restricted Antigens in the Endoplasmic Reticulum," The Journal of Experimental Medicine, 181:1481–1491, Apr. 1995.

Donnelly et al., "immunization with DNA," Journal of Immunological Methods, 176:145–152, No. 2, 1994.

Feltkamp et al., "Vaccination with cytotoxic T Lymphocyte epitope–containing peptide protects against a tumor induced by human papillomavirus type 16–transformed cells," European Journal of Immunology, 23:2242–2249, 1993.

Fries et al., "Liposomal Malaria Vaccine in Humans: A Safe and Potent adjuvant Strategy," Proceedings of The National Academy of Sciences, 89:358–362, Jan. 1992.

Fynan et al., "DNA Vaccines: Protective Immunizations by Parenteral, Mucosal, and Gene–Gun Inoculations," Proceedings of The National Academy of Sciences, 90:11478–11482, 1993.

Gao et al., "Tumor–Associated E6 Protein of Human Papillomavirus Type 16 Contains an Unusual $H–2K^b$–Restricted Cytotoxic T Cell Epitope," The Journal of Immunology, 155:5519–5526, 1995.

Hurtenbach et al., "Prevention of Autoimmune Diabetes in Non–Obese Diabetic Mice by Treatment with a Class II Major Histocompatibility Complex–blocking Peptide," The Journal of Experimental Medicine, 177:1499–1504, 1993.

Jochmus et al., "Specificity of human cytotoxic T Lymphocytes induced by a human papillomavirus type 16 E7–derived peptide," The Journal of General Virology, 78:1689–1695, 1997.

(List continued on next page.)

Primary Examiner—Ali R. Salimi
(74) Attorney, Agent, or Firm—Fish & Richardson P.C.

(57) ABSTRACT

The invention provides immunogenic peptides from the HPV type 16 E7 protein that comprise overlapping class I restricted T cell epitopes. Also disclosed are methods of administering DNA molecules encoding these peptides to a host mammal.

28 Claims, 3 Drawing Sheets

OTHER PUBLICATIONS

Kadish et al., "Cell–mediated immune responses to E7 peptides of human papillomavirus (HPV) type 16 are dependent on the HPV type infecting the cervix whereas serological reactivity is not type–specific," The Journal of General Viology, 75:2277–2284, 1994.

Kadish et al., "Lymphoproliferative Responses to Human Papillomavirus (HPV) Type 16 Proteins E6 and E7: Outcome of HPV Infection and Associated Neoplasia," Journal of The National Cancer Institute, 89:1285, 1997.

Kast et al., "Human Leukocyte Antien–A2.1 Restricted Candidate Cytotoxic T Lymphocyte Epitopes of Human Papillomavirus Type 16 E6 and E7 Proteins Identified by Using the Processing–Defective Human Cell Line T2," The Journal of Immunotherapy, 14:115–120, 1993.

Kast et al., "Role of HLA–A Motifs in Identification of Potential CTL Epitopes in Human Papillomavirus Type 16 E6 and E7 Proteins," The Journal of Immunology, 152:3904–3912, 1994.

Lin et al., "Treatment of Established Tumors with a Novel Vaccine that Enhances Major Histocompatibility Class II Presentation of Tumor Antigen," Cancer Research, 56:21–26, 1996.

Madden et al., "The Antigenic Identity of Peptide–MHC Complexes: A Comparison of the conformations of Five Viral Peptides Presented by HLA–A2," Cell, 75:693–708, Nov 19, 1993.

Mowat et al., "ISCOMS—A Novel Strategy for Mucosal Immunization?", Immunology Today, 12:383–385, 1991.

Nabel et al., "Transduction of a Foreign Histocompatibility Gene into the Arterial Wall Induces Vasculitis," Proceedings of The National Academy of Sciences, 89:5157–5161, No. 11, Jun. 1992.

Osband et al., "Problems in the Investigational Study and Clinical Use of Cancer Immunotherapy," Immunology Today, 11:193–195, 1990.

Reddy et al., "In Vivo Cytotoxic T Lymphocyte Induction with Soluble Proteins Administered in Liposomes," The Journal of Immunology, 148:1585–1589, No. 5, Mar. 1992.

Ressing et al., "Occasional Memory Cytotoxic T–Cell Responses of Patients with Human Papillomavirus Type 16–positive Cervical Lesions against a Human Leukocyte Antigen–A 0201–restricted E7–encoded Epitope," Cancer Research, 56:582–588, Feb. 1, 1996.

Ressing et al., "human CTL Epitopes Encoded by Human Papillomavirus Type 16 E6 and E7 Identified Through In Vivo and In Vitro Immunogenicity Studies of HLA–A 0201 Binding Peptides," The Journal of Immunology, 154:5934–5943, Jun. 1, 1995.

Shrine et al., "Pangaea Aims Naturally Processed Peptides at First viral Target: Human Papilloma Virus," Bioworld Today, The Biotechnology Newspaper, 7:1–2, May 15, 1996.

Stellar et al., "Human Papillomavirus Immunology and Vaccine Prospects," Journal of The National Cancer Institute Monographs, No. 21, 1996, pp. 145–148.

Takahashi et al., "Induction of CD8 Cytotoxic T Cells by Immunization with Purified HIV–1 Envelope Protein in ISCOMs," Nature, 344:873–875, Apr. 1990.

Tarpey et al., "Human Cytotoxic T Lymphocytes Stimulated by Endogenously processed human papillomavirus type 11 E7 recognize a peptide containing a HLA–A2 (A*0201) motif," Immunology, 81:222–227, 1994.

Tsukui et al., "Interleukin 2 Production in vitro by Peripheral Lymphocytes in response to Human Papillomavirus–derived peptides: Correlation with Cervical Pathology," Cancer Research, 56:3855–4085, 1996.

Urban et al., "A subset of HLA–B27 Molecules contains peptides much longer than nonamers," Proceedings of The National Academy of Sciences, 91:1534–1538, Feb. 1994.

Vitiello et al., Development of a Lipopeptide Based Therapeutic Vaccine to Treat chronic HBV Infection, The Journal of Clinical Investigation, 95:341–349, Jan. 1995.

Vitiello et al., "Analysis of the HLA–restricted Influenza–specific Cytotoxic T Lymphocyte Response in Transgenic Mice Carrying a Chimeric Human–Mouse Class I Major Histocompatibility Complex," J. Exp. Med., 173:1007–1015, Apr. 1991.

Zhu et al., "Both Immunization with Protein and Recombinant Vaccinia Virus Can Stimulate CTL Specific for the E7 Protein of Human Papilloma Virus 16 in $H-2^d$ Mice," Scandinavian Journal of Immunology, 42:557–563, 1995.

* cited by examiner

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
       (A) LENGTH: 9 amino acids
       (B) TYPE: amino acid
       (D) TOPOLOGY: linear (ii) MOLECULE TYPE: peptide (xi) SEQUENCE DESCRIPTION: SEQ ID NO:1:

Leu Leu Met Gly Thr Leu Gly Ile Val
 1               5

(2) INFORMATION FOR SEQ ID NO:2:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:2:

```
Thr Leu Gly Ile Val Cys Pro Ile Cys
 1               5
```

(2) INFORMATION FOR SEQ ID NO:3:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:3:

```
Leu Leu Met Gly Thr Leu Gly Ile Val Cys Pro Ile Cys
 1               5                  10
```

(2) INFORMATION FOR SEQ ID NO:4:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:4:

```
Ala Leu Met Gly Thr Leu Gly Ile Val Cys Pro Ile Cys
 1               5                  10
```

(2) INFORMATION FOR SEQ ID NO:5:

(i) SEQUENCE CHARACTERISTICS:
        (A) LENGTH: 117 base pairs
        (B) TYPE: nucleic acid
        (C) STRANDEDNESS: double
        (D) TOPOLOGY: linear (ii) MOLECULE TYPE: DNA (ix) FEATURE:
        (A) NAME/KEY: Coding Sequence
        (B) LOCATION: 1...114

(xi) SEQUENCE DESCRIPTION: SEQ ID NO:5:

```
ATG GCC ATA AGT GGA GTC CCT GTG CTA GGA TTT TTC ATC ATA GCT GTG    48
Met Ala Ile Ser Gly Val Pro Val Leu Gly Phe Phe Ile Ile Ala Val
 1               5                  10                  15

CTG ATG AGC GCT CAG GAA TCA TGG GCT GCC CTG ATG GGC ACC CTG GGC    96
Leu Met Ser Ala Gln Glu Ser Trp Ala Ala Leu Met Gly Thr Leu Gly
                 20                  25                  30

ATC GTG TGC CCC ATC TGC TGA                                       117
Ile Val Cys Pro Ile Cys
                 35
```

(2) INFORMATION FOR SEQ ID NO:6:

(i) SEQUENCE CHARACTERISTICS:
        (A) LENGTH: 38 amino acids (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:6:

Met Ala Ile Ser Gly Val Pro Val Leu Gly Phe Phe Ile Ile Ala Val
 1               5                  10                  15

Leu Met Ser Ala Gln Glu Ser Trp Ala Ala Leu Met Gly Thr Leu Gly
                20                  25                  30

Ile Val Cys Pro Ile Cys
            35

(2) INFORMATION FOR SEQ ID NO:7:

(i) SEQUENCE CHARACTERISTICS:
        (A) LENGTH: 4665 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:7:

```
GCACTTTTCG GGGAAATGTG CGCGGAACCC CTATTTGTTT ATTTTTCTAA ATACATTCAA     60
ATATGTATCC GCTCATGAGA CAATAACCCT GATAAATGCT TCAATAATAT TGAAAAAGGA    120
AGAGTCCTGA GGCGGAAAGA ACCAGCTGTG GAATGTGTGT CAGTTAGGGT GTGGAAAGTC    180
CCCAGGCTCC CCAGCAGGCA GAAGTATGCA AAGCATGCAT CTCAATTAGT CAGCAACCAG    240
GTGTGGAAAG TCCCCAGGCT CCCCAGCAGG CAGAAGTATG CAAAGCATGC ATCTCAATTA    300
GTCAGCAACC ATAGTCCCGC CCCTAACTCC GCCCATCCCG CCCCTAACTC CGCCCAGTTC    360
CGCCCATTCT CCGCCCCATG GCTGACTAAT TTTTTTTATT TATGCAGAGG CCGAGGCCGC    420
CTCGGCCTCT GAGCTATTCC AGAAGTAGTG AGGAGGCTTT TTTGGAGGCC TAGGCTTTTG    480
CAAAGATCGA TCAAGAGACA GGATGAGGAT CGTTTCGCAT GATTGAACAA GATGGATTGC    540
ACGCAGGTTC TCCGGCCGCT TGGGTGGAGA GGCTATTCGG CTATGACTGG GCACAACAGA    600
CAATCGGCTG CTCTGATGCC GCCGTGTTCC GGCTGTCAGC GCAGGGGCGC CCGGTTCTTT    660
TTGTCAAGAC CGACCTGTCC GGTGCCCTGA ATGAACTGCA AGACGAGGCA GCGCGGCTAT    720
CGTGGCTGGC CACGACGGGC GTTCCTTGCG CAGCTGTGCT CGACGTTGTC ACTGAAGCGG    780
GAAGGGACTG GCTGCTATTG GGCGAAGTGC CGGGGCAGGA TCTCCTGTCA TCTCACCTTG    840
CTCCTGCCGA GAAAGTATCC ATCATGGCTG ATGCAATGCG GCGGCTGCAT ACGCTTGATC    900
CGGCTACCTG CCCATTCGAC CACCAAGCGA AACATCGCAT CGAGCGAGCA CGTACTCGGA    960
TGGAAGCCGG TCTTGTCGAT CAGGATGATC TGGACGAAGA GCATCAGGGG CTCGCGCCAG   1020
CCGAACTGTT CGCCAGGCTC AAGGCGAGCA TGCCCGACGG CGAGGATCTC GTCGTGACCC   1080
ATGGCGATGC CTGCTTGCCG AATATCATGG TGGAAAATGG CCGCTTTTCT GGATTCATCG   1140
ACTGTGGCCG GCTGGGTGTG GCGGACCGCT ATCAGGACAT AGCGTTGGCT ACCCGTGATA   1200
TTGCTGAAGA GCTTGGCGGC GAATGGGCTG ACCGCTTCCT CGTGCTTTAC GGTATCGCCG   1260
CTCCCGATTC GCAGCGCATC GCCTTCTATC GCCTTCTTGA CGAGTTCTTC TGAGCGGGAC   1320
TCTGGGGTTC GAAATGACCG ACCAAGCGAC GCCCAACCTG CCATCACGAG ATTTCGATTC   1380
CACCGCCGCC TTCTATGAAA GGTTGGGCTT CGGAATCGTT TTCCGGGACG CCGGCTGGAT   1440
```

```
GATCCTCCAG CGCGGGGATC TCATGCTGGA GTTCTTCGCC CACCCTAGGG GGAGGCTAAC    1500

TGAAACACGG AAGGAGACAA TACCGGAAGG AACCCGCGCT ATGACGGCAA TAAAAAGACA    1560

GAATAAAACG CACGGTGTTG GGTCGTTTGT TCATAAACGC GGGGTTCGGT CCCAGGGCTG    1620

GCACTCTGTC GATACCCCAC CGAGACCCCA TTGGGGCCAA TACGCCCGCG TTTCTTCCTT    1680

TTCCCCACCC CACCCCCCAA GTTCGGGTGA AGGCCCAGGG CTCGCAGCCA ACGTCGGGGC    1740

GGCAGGCCCT GCCATAGCCT CAGGTTACTC ATATATACTT TAGATTGATT TAAAACTTCA    1800

TTTTTAATTT AAAAGGATCT AGGTGAAGAT CCTTTTTGAT AATCTCATGA CCAAAATCCC    1860

TTAACGTGAG TTTTCGTTCC ACTGAGCGTC AGACCCCGTA GAAAAGATCA AAGGATCTTC    1920

TTGAGATCCT TTTTTTCTGC GCGTAATCTG CTGCTTGCAA ACAAAAAAAC CACCGCTACC    1980

AGCGGTGGTT TGTTTGCCGG ATCAAGAGCT ACCAACTCTT TTTCCGAAGG TAACTGGCTT    2040

CAGCAGAGCG CAGATACCAA ATACTGTTCT TCTAGTGTAG CCGTAGTTAG GCCACCACTT    2100

CAAGAACTCT GTAGCACCGC CTACATACCT CGCTCTGCTA ATCCTGTTAC CAGTGGCTGC    2160

TGCCAGTGGC GATAAGTCGT GTCTTACCGG GTTGGACTCA AGACGATAGT TACCGGATAA    2220

GGCGCAGCGG TCGGGCTGAA CGGGGGGTTC GTGCACACAG CCCAGCTTGG AGCGAACGAC    2280

CTACACCGAA CTGAGATACC TACAGCGTGA GCTATGAGAA AGCGCCACGC TTCCCGAAGG    2340

GAGAAAGGCG GACAGGTATC CGGTAAGCGG CAGGGTCGGA ACAGGAGAGC GCACGAGGGA    2400

GCTTCCAGGG GGAAACGCCT GGTATCTTTA TAGTCCTGTC GGGTTTCGCC ACCTCTGACT    2460

TGAGCGTCGA TTTTTGTGAT GCTCGTCAGG GGGCGGAGC CTATGGAAAA ACGCCAGCAA    2520

CGCGGCCTTT TTACGGTTCC TGGCCTTTTG CTGGCCTTTT GCTCACATGT TCTTTCCTGC    2580

GTTATCCCCT GATTCTGTGG ATAACCGTAT TACCGCCATG CATTAGTTAT TAATAGTAAT    2640

CAATTACGGG GTCATTAGTT CATAGCCCAT ATATGGAGTT CCGCGTTACA TAACTTACGG    2700

TAAATGGCCC GCCTGGCTGA CCGCCCAACG ACCCCCGCCC ATTGACGTCA ATAATGACGT    2760

ATGTTCCCAT AGTAACGCCA ATAGGGACTT TCCATTGACG TCAATGGGTG GAGTATTTAC    2820

GGTAAACTGC CCACTTGGCA GTACATCAAG TGTATCATAT GCCAAGTACG CCCCCTATTG    2880

ACGTCAATGA CGGTAAATGG CCCGCCTGGC ATTATGCCCA GTACATGACC TTATGGGACT    2940

TTCCTACTTG GCAGTACATC TACGTATTAG TCATCGCTAT TACCATGGTG ATGCGGTTTT    3000

GGCAGTACAT CAATGGGCGT GGATAGCGGT TTGACTCACG GGGATTTCCA AGTCTCCACC    3060

CCATTGACGT CAATGGGAGT TTGTTTTGGC ACCAAAATCA ACGGGACTTT CCAAAATGTC    3120

GTAACAACTC CGCCCCATTG ACGCAAATGG GCGGTAGGCG TGTACGGTGG GAGGTCTATA    3180

TAAGCAGAGC TGGTTTAGTG AACCGTCAGA TCCGCTAGAG CTTGCTTGTT CTTTTTGCAG    3240

AAGCTCAGAA TAAACGCTCA ACTTTGGCAG ATCCGCGGCT CGAGCCACCA TGGACATGGC    3300

CATAAGTGGA GTCCCTGTGC TAGGATTTTT CATCATAGCT GTGCTGATGA GCGCTCAGGA    3360

ATCATGGGCT GCCCTGATGG GCACCCTGGG CATCGTGTGC CCCATCTGCT GAGCTCCTGG    3420

AATTCGGATC TGGTTACCAC TAAACCAGCC TCAAGAACAC CCGAATGGAG TCTCTAAGCT    3480

ACATAATACC AACTTACACT TTACAAAATG TTGTCCCCCA AAATGTAGCC ATTCGTATCT    3540

GCTCCTAATA AAAAGAAAGT TTCTTCACAT TCTAAAAAAA AAAAAAAAA AAAAAAAAA    3600

AAAAACCCC CCCCCCCCC CCCCATCGAT TTTCCACCCG GGTGGGGTAC CAGGTAAGTG    3660

TACCCAATTC GCCCTATAGT GAGTCGTATT ACAATTCACT GGCCGTCGTT TTACAACGTC    3720

GTGACTGGGA AAACCCTGGC GTTACCCAAA TTAATCGCCT TGCAGCACAT CCCCCTTTCG    3780

CCAGCTGGCG TAATAGCGAA GAGGCCCGCA CCGATCGCCC TTCCCAACAG TTGCGCAGCC    3840
```

```
TGAATGGCGA ATGGAGATCC AATTTTTAAG TGTATAATGT GTTAAACTAC TGATTCTAAT       3900

TGTTTGTGTA TTTTAGATTC ACAGTCCCAA GGCTCATTTC AGGCCCCTCA GTCCTCACAG       3960

TCTGTTCATG ATCATAATCA GCCATACCAC ATTTGTAGAG GTTTTACTTG CTTTAAAAAA       4020

CCTCCCACAC CTCCCCCTGA ACCTGAAACA TAAAATGAAT GCAATTGTTG TTGTTAACTT       4080

GTTTATTGCA GCTTATAATG GTTACAAATA AAGCAATAGC ATCACAAATT TCACAAATAA       4140

AGCATTTTTT TCACTGCATT CTAGTTGTGG TTTGTCCAAA CTCATCAATG TATCTTAACG       4200

CGTAAATTGT AAGCGTTAAT ATTTTGTTAA AATTCGCGTT AAATTTTTGT TAAATCAGCT       4260

CATTTTTTAA CCAATAGGCC GAAATCGGCA AAATCCCTTA TAAATCAAAA GAATAGACCG       4320

AGATAGGGTT GAGTGTTGTT CCAGTTTGGA ACAAGAGTCC ACTATTAAAG AACGTGGACT       4380

CCAACGTCAA AGGGCGAAAA ACCGTCTATC AGGGCGATGG CCCACTACGT GAACCATCAC       4440

CCTAATCAAG TTTTTTGGGG TCGAGGTGCC GTAAAGCACT AAATCGGAAC CCTAAAGGGA       4500

GCCCCCGATT TAGAGCTTGA CGGGGAAAGC CGGCGAACGT GGCGAGAAAG GAAGGGAAGA       4560

AAGCGAAAGG AGCGGGCGCT AGGGCGCTGG CAAGTGTAGC GGTCACGCTG CGCGTAACCA       4620

CCACACCCGC CGCGCTTAAT GCGCCGCTAC AGGGCGCGTC AGGTG                      4665
```

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

```
GGCGTCGACA TGGCCATAAG TGGAGTC                                           27
```

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

```
GAAGCTGGCA GCCCATGATT CCTGAGC                                           27
```

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

```
TCATGGGCTG CCAGCTTCGA GGCCCAG                                           27
```

(2) INFORMATION FOR SEQ ID NO:11:

(i) SEQUENCE CHARACTERISTICS:
        (A) LENGTH: 27 base pairs (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

CGGGAATTCT TAGGCCTTGT CCACGGC                                              27

(2) INFORMATION FOR SEQ ID NO:12:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

ATCAGCGCTC AGGAATCATG GGCTGCCCTG GGCATCGTGT GCCCCATCTG CTGAGCTCGA          60

G                                                                          61

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

GGGGATCCGA ATTCCTCGAG CTCA                                                 24

(2) INFORMATION FOR SEQ ID NO:14:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

ATCAGCGCTC AGGAATCATG GGCTCTGATG GGCACCCTGG GCATCGTGTG CCCCATCTGC          60

TGAGCTCGAG                                                                 70

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

GGGGATCCGA ATTCCTCGAG CTCA                                                 24

(2) INFORMATION FOR SEQ ID NO:16:

(i) SEQUENCE CHARACTERISTICS:
        (A) LENGTH: 12 amino acids

```
        (B) TYPE: amino acid
        (D) TOPOLOGY: linear (ii) MOLECULE TYPE: peptide (xi) SEQUENCE DESCRIPTION: SEQ ID NO:16:

Leu Met Gly Thr Leu Gly Ile Val Cys Pro Ile Cys
 1               5                  10

(2) INFORMATION FOR SEQ ID NO:17:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:17:

Tyr Met Leu Asp Leu Gln Pro Glu Thr
 1               5

(2) INFORMATION FOR SEQ ID NO:18:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO:18:

Met Ala Ile Ser Gly Val Pro Val Leu Gly Phe Phe Ile Ile Ala Val
 1               5                  10                  15

Leu Met Ser Ala Gln Glu Ser Trp Ala
                20                  25

(2) INFORMATION FOR SEQ ID NO:19:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: where Xaa at position 1 is Met, Ala,
            Ser, Arg, Lys, Gly, Gln, Asp, or Glu (xi) SEQUENCE DESCRIPTION: SEQ ID NO:19:

Xaa Leu Met Gly Thr Leu Gly Ile Val Cys Pro Ile Cys
 1               5                  10

(2) INFORMATION FOR SEQ ID NO:20:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:20:

Thr Leu Gly Ile Val Cys Pro Ile
 1               5
```

(2) INFORMATION FOR SEQ ID NO:21:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:21:

```
Gly Thr Leu Gly Ile Val Cys Pro Ile
 1               5
```

(2) INFORMATION FOR SEQ ID NO:22:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:22:

```
Ile Val Cys Pro Ile Cys Ser Gln Lys
 1               5
```

(2) INFORMATION FOR SEQ ID NO:23:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:23:

```
Lys Asp Glu Leu
 1
```

(2) INFORMATION FOR SEQ ID NO:24:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:24:

```
Gly Ile Leu Gly Phe Val Phe Thr Leu
 1               5
```

(2) INFORMATION FOR SEQ ID NO:25:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:25:

```
Leu Leu Met Gly Thr Leu Gly Ile Val Cys Pro Ile Cys Ser Gln Lys
 1               5                  10                  15
```

(2) INFORMATION FOR SEQ ID NO:26:

(i) SEQUENCE CHARACTERISTICS:

(A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:26:

Met Gly Ile Val Cys Pro Ile Cys
 1               5

(2) INFORMATION FOR SEQ ID NO:27:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: where Xaa at position 1 is Met, Ala,
            Ser, Arg, Lys, Gly, Gln, Asp, or Glu (xi) SEQUENCE DESCRIPTION: SEQ ID NO:27:

Xaa Thr Leu Gly Ile Val Cys Pro Ile
 1               5

(2) INFORMATION FOR SEQ ID NO:28:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:28:

Gly Thr Leu Gly Leu Gly Ile Val Cys Pro Ile
 1               5                   10

(2) INFORMATION FOR SEQ ID NO:29:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:29:

Lys Phe Glu Arg Gln
 1               5

(2) INFORMATION FOR SEQ ID NO:30:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:30:

Gln Phe Glu Phe Lys
 1               5

(2) INFORMATION FOR SEQ ID NO:31:

```
        (i) SEQUENCE CHARACTERISTICS:
              (A) LENGTH: 11 amino acids
              (B) TYPE: amino acid
              (D) TOPOLOGY: linear (ii) MOLECULE TYPE: peptide (ix) FEATURE:
              (A) NAME/KEY: Other
              (B) LOCATION: 1...1
              (D) OTHER INFORMATION: where Xaa at position 1 is Met,
                   Ala, Ser, Arg, Lys, Gly, Gln, Asp, or Glu (xi) SEQUENCE DESCRIPTION: SEQ ID NO:31:

Xaa Gly Thr Leu Gly Ile Val Cys Pro Ile Cys
 1               5                      10

(2) INFORMATION FOR SEQ ID NO:32:

(i) SEQUENCE CHARACTERISTICS:
              (A) LENGTH: 14 amino acids
              (B) TYPE: amino acid
              (D) TOPOLOGY: linear (ii) MOLECULE TYPE: peptide (xi) SEQUENCE DESCRIPTION: SEQ ID NO:32:

Met Gly Thr Leu Gly Ile Val Cys Pro Ile Cys Ser Gln Lys
 1               5                      10

(2) INFORMATION FOR SEQ ID NO:33:

(i) SEQUENCE CHARACTERISTICS:
              (A) LENGTH: 11 amino acids
              (B) TYPE: amino acid
              (D) TOPOLOGY: linear (ii) MOLECULE TYPE: peptide (xi) SEQUENCE DESCRIPTION: SEQ ID NO:33:

Met Gly Thr Leu Gly Ile Val Cys Pro Ile Cys
 1               5                      10
```

IMMUNOGENIC PEPTIDES FROM THE HPV E7 PROTEIN

CROSS REFERENCE TO RELATED APPLICATIONS

This application is a divisional application of U.S. application Ser. No. 09/169,425, filed on Oct. 9, 1998, issued as U.S. Pat. No. 6,183,746, on Feb. 6, 2001, which claims priority from U.S. Application Serial No. 60/061,657, filed on Oct. 9, 1997. The content of these applications is incorporated by reference.

BACKGROUND OF THE INVENTION

This invention relates to treatment of human papilloma virus (HPV) infection.

Papilloma viruses are non-enveloped DNA viruses with a double stranded circular genome of approximately 8,000 bp. Over 75 types of human papilloma viruses (HPV) have been typed at the DNA level, and these can be broadly grouped into families on the basis of their tissue tropism.

Histologic, molecular, and epidemiologic evidence have implicated some HPV strains in cervical dysplasia and cervical cancer. Many studies support the view that most moderate and severe cervical intraepithelial neoplasias (CIN) contain HPV DNA which is exclusively detected in the histologically abnormal epithelium of these lesions. Persistent infection with HPV is believed to be the predominant risk factor for development of cervical carcinoma. HPV DNA is readily found in episomal form within cells exhibiting a cytopathic effect, while the HPV DNA is found integrated within the chromosomes of cells associated with most high grade precancerous lesions and cancer. Approximately 23 HPV types are commonly found in anogenital screening programs, but only 10–15 are associated with progressive disease. Type 16 is the type most commonly found in cervical cancer tissue.

Papillomaviruses contain nine open reading frames. HPV genes with transforming properties have been mapped to open reading frames E6 and E7. Substantial biochemical work has demonstrated that the HPV E6 protein inactivates the protein p53, whereas the E7 protein interferes with retinoblastoma (Rb) protein function. Since p53 and Rb are tumor-suppressor proteins which function as cell division inhibitors, their inactivation by E6 and E7 leads the cell to enter into S phase of the cell cycle. Expression of E6 and E7 is sufficient to immortalize some primary cell lines, and blocking E6 or E7 function has been shown to reverse the transformed state.

SUMMARY OF THE INVENTION

The invention is based on the discovery that a 13 amino acid peptide from the HPV strain 16 E7 protein that contains overlapping class I HLA binding, T cell epitopes can induce a CTL response in an animal. Accordingly, the invention includes an immunogenic peptide having within its sequence multiple class I MHC-binding epitopes from a human papillomavirus (HPV) protein, and which has a length of less than 19 amino acids and includes the sequence of Leu Met Gly Thr Leu Gly Ile Val Cys Pro Ile Cys (SEQ ID NO:16) (hereinafter "immunogenic peptide"). The immunogenic peptide can optionally include sequences in addition to those derived from the E7 protein.

The immunogenic peptide can have the sequence of Leu Leu Met Gly Thr Leu Gly Ile Val Cys Pro Ile Cys (SEQ ID NO:3) or Xaa Leu Met Gly Thr Leu Gly Ile Val Cys Pro Ile Cys, Xaa being Met, Ala, Ser, Arg, Lys, Gly, Gln, Asp, or Glu (SEQ ID NO:19), e.g., Ala Leu Met Gly Thr Leu Gly Ile Val Cys Pro Ile Cys (SEQ ID NO:4).

The invention also includes the peptides Thr Leu Gly Ile Val Cys Pro Ile (SEQ ID NO:20) and Gly Thr Leu Gly Ile Val Cys Pro Ile (SEQ ID NO:21), as well as Xaa Thr Leu Gly Ile Val Cys Pro Ile (SEQ ID NO:27) and Gly Thr Leu Gly Leu Gly Ile Val Cys Pro Ile (SEQ ID NO:28), Xaa being Met, Ala, Ser, Arg, Lys, Gly, Gln, Asp, or Glu.

In addition, all of the peptides discussed herein may include additional amino acids to facilitate expression, e.g., an amino terminal methionine to facilitate translation.

The invention also includes a polypeptide having the sequence of a first peptide linked to a second peptide by a peptide bond. The first peptide (which can be at the carboxy terminus or the amino terminus of the second peptide, so long as it functions in that site) is a peptide which controls intracellular trafficking of a peptide to which it is attached, and the second peptide is the immunogenic peptide described above. The polypeptide may optionally be modified to introduce an amino acid substitution at the junction between the first and second peptides to promote cleavage of the first and second peptides by a signal peptidase.

The trafficking peptides can be any recognized signal sequence, e.g. a signal sequence from the adenovirus E3 protein. A preferred trafficking peptide is the signal peptide of HLA-DRα, Met Ala Ile Ser Gly Val Pro Val Leu Gly Phe Phe Ile Ile Ala Val Leu Met Ser Ala Gln Glu Ser Trp Ala (SEQ ID NO:18).

The invention in addition includes a therapeutic composition containing the immunogenic peptide described above, and a pharmaceutically acceptable carrier. The polypeptide can optionally be formulated in a microparticle, a liposome or an immune-stimulating complex (ISCOM) (which may contain saponin alone as the active ingredient), or any other vehicle suitable for delivering into subjects the immunogenic peptides of the invention. When a microparticle is used, it preferably has a polymeric matrix that is a copolymer such as poly-lactic-co-glycolic acid (PLGA).

An immune response (e.g., a cellular immune response, including an MHC class I-mediated or class II-mediated immune response) in a mammal can be elicited by administering the immunogenic peptide to a mammal, e.g., a human, non-human primate, dog, cat, rabbit, cow, mouse, rat, guinea pig, or hamster, that has an MHC molecule that binds to the immunogenic peptide. The immunogenic peptide can be administered as part of a microparticle, liposome, or ISCOM, or in solution.

Another way to administer the peptide utilizes a nucleic acid, e.g., an expression vector, comprising a coding sequence encoding the immunogenic peptide. The nucleic acid can optionally encode a signal sequence linked to the immunogenic peptide, as described above. When the nucleic acid encodes such a signal sequence, it is preferred that it encodes the signal sequence from HLA-DRα (SEQ ID NO:18). In such a case, the immunogenic peptide can have the sequence, for example, of SEQ ID NO:4 or SEQ ID NO:3. Preferably, the nucleic acid does not include sequences from a viral genome that would render the nucleic acid infectious, and does not encode an intact E7 protein.

The nucleic acid described above can be included in a plasmid, optionally provided in a microparticle that also includes a polymeric matrix. In preferred embodiments, the polymeric matrix consists essentially of a copolymer of PLGA. The microparticle preferably has a diameter of, e.g., 0.02 to 20 microns, or less than about 11 microns. A plurality of microparticles preferably has diameter of, e.g., 0.02 to 20 microns, or less than about 11 microns Also within the invention is a cell containing the plasmid of the invention. The cell can, e.g., be a B cell or other antigen presenting cell (APC). The cell may be cultured or otherwise maintained under conditions permitting expression of the peptide from the plasmid encoding it.

The nucleic acid and plasmid of the invention are useful in a method of inducing an immune response in a mammal, e.g., a human, by administering the above-described plasmid to the mammal, e.g., as "naked DNA". The mammal may be at risk for, or suffer from, HPV infection, cervical dysplasia, and/or cervical cancer. The nucleic acids and plasmids of the invention can also be incorporated into microparticles, liposomes, ISCOMS, or any other suitable delivery vehicle as described above.

The invention further includes a plasmid having a sequence essentially identical to that of pBIOTOPE$_{HPV}$ (SEQ ID NO:7), or a microparticle consisting essentially of a PLGA polymeric matrix and the pBIOTOPE$_{HPV}$ plasmid, as well as methods of inducing an immune response in a mammal by administering either the plasmid alone, or the plasmid incorporated into such a microparticle, to the mammal.

By a "substantially pure polypeptide" is meant a polypeptide which is separated from those components (proteins and other naturally-occurring organic molecules) which naturally accompany it. Typically, the polypeptide is substantially pure when it constitutes at least 60%, by weight, of the protein in the preparation. Preferably, the protein in the preparation consists of at least 75%, more preferably at least 90%, and most preferably at least 99%, by weight, of an immunogenic peptide.

Unless otherwise defined, all technical and scientific terms used herein have the same meaning as commonly understood by one of ordinary skill in the art to which this invention belongs. The preferred methods and materials for practicing the invention are described below, although other methods and materials similar or equivalent to those described herein can be used in the practice or testing of the present invention. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

DETAILED DESCRIPTION

Figure 1:
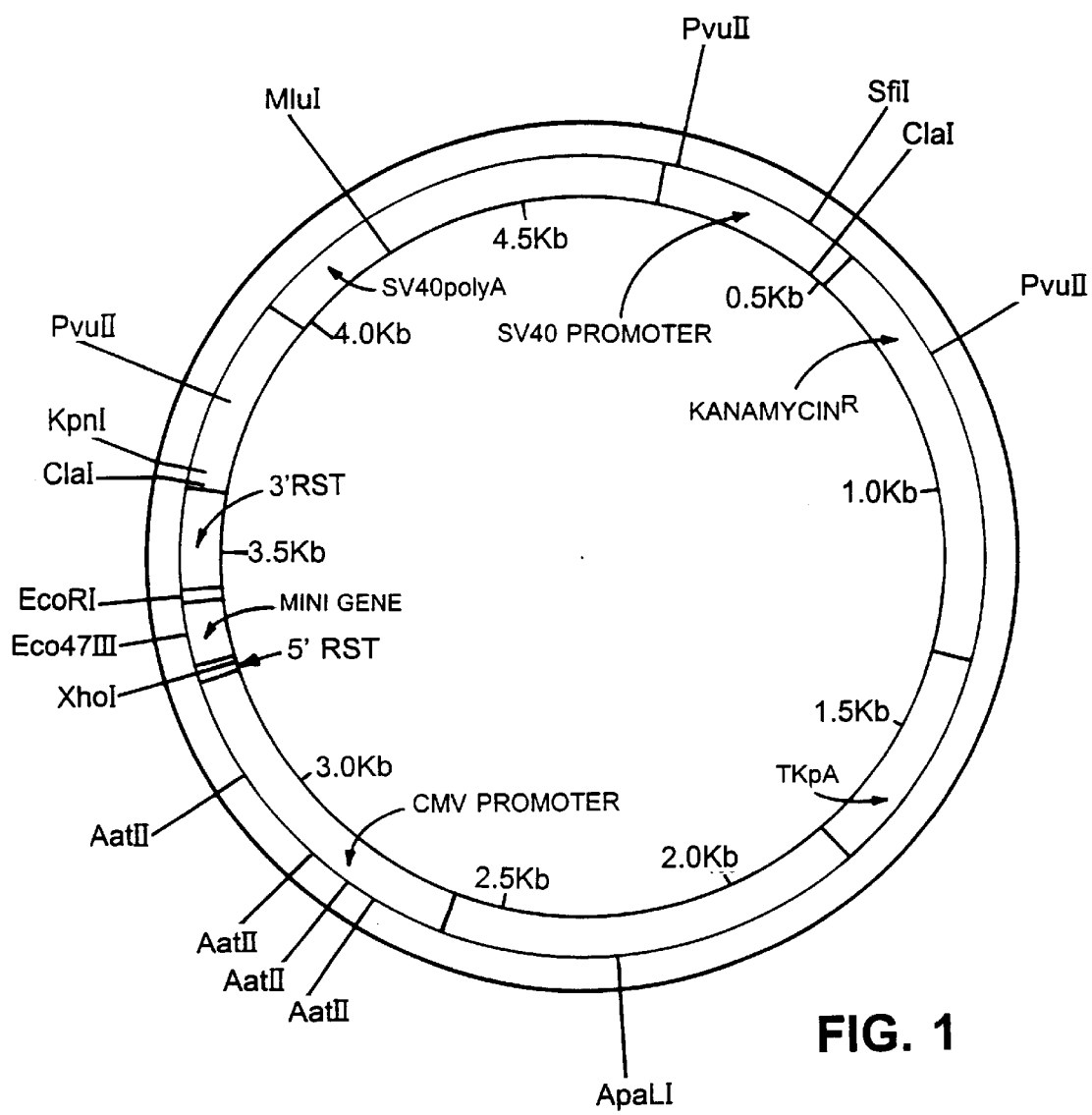
FIG. 1 is a schematic drawing of the pBIOTOPE$_{HPV}$ plasmid.

The peptides disclosed herein, and the nucleic acids encoding the peptides, can be used to elicit an immune response against the HPV E7 protein. The peptides were identified in part based on their binding affinity with the MHC class I HLA-A2 allele. Thus, the immune response elicited by these peptides is likely to be class I-mediated but may also involve class II mediated responses, B cell responses, or NK cell responses. The immune response can thus involve, e.g., cells expressing MHC class I molecules or cells expressing MHC class II molecules. The immune response can also include immune cells such as macrophages, polymorphonuclear monocytes (PMN), natural killer cells, and B cells.

Five immunogenic peptides derived from the HPV type 16 E7 protein are shown in Table I. Peptide A2.1/4, Leu Leu Met Gly Thr Leu Gly Ile Val Cys Pro Ile Cys (SEQ ID NO:3), corresponds to amino acids 82–94 in the HPV Type 16 E7 protein and includes the overlapping sequences of peptides A2.1, Leu Leu Met Gly Thr Leu Gly Ile Val (SEQ ID NO:1), A2.4, Thr Leu Gly Ile Val Cys Pro Ile Cys (SEQ ID NO:2) A2.4-C, Thr Leu Gly Ile Val Cys Pro Ile (SEQ ID NO:20), and A2.5, Gly Thr Leu Gly Ile Val Cys Pro Ile (SEQ ID NO:21). Thus, peptide A2.1/4 has at least four overlapping epitopes potentially recognized by class I MHC restricted T cells.

TABLE I

Amino acid sequences of conserved, class I-MHC binding, TCR binding HPV strain 16 E7 peptides

| A2.1 | LLMGTLGIV | (SEQ ID NO: 1) |
| A2.4 | TLGIVCPIC | (SEQ ID NO: 2) |
| A2.1/4 | LLMGTLGIVCPIC | (SEQ ID NO: 3) |
| A2.4-C | TLGIVCPI | (SEQ ID NO: 20) |
| A2.5 | GTLGIVCPI | (SEQ ID NO: 21) |

A peptide of the invention may optionally include one having the amino acids SQK added to the carboxy terminus of the A2.1/4 peptide sequence ("the extended peptide"). Processing of the extended peptide can generate the peptide IVCPICSQK (SEQ ID NO:22), which has been reported as binding the MHC class I molecules HLA-A3 and HLA-A11 (Kast et al., J. Immunol. 152:3904–11, 1994). This region of the HPV E7 protein has several peptides that can be processed into MHC binding peptides. Additional extensions to the amino or carboxy terminus of the A2.1/4 peptide may further increase the number of peptides that can be generated from this region of the E7 protein.

The peptides of the invention can be linked to a trafficking sequence that directs the peptides to a desired intracellular compartment. A trafficking sequence is an amino acid sequence which functions to control intracellular trafficking (directed movement from organelle to organelle or to the cell surface) of a polypeptide to which it is attached. Such trafficking sequences might traffic the polypeptide to ER, a lysosome, or an endosome, and include signal peptides (the amino terminal sequences which direct proteins into the ER during translation), ER retention peptides such as KDEL (SEQ ID NO:23), and lysosome-targeting peptides such as KFERQ (SEQ ID NO:29), QREFK (SEQ ID NO:30), and other pentapeptides having Q flanked on one side by four residues selected from K, R, D, E, F, I, V, and L.

Short amino acid sequences can act as signals to target proteins to specific intracellular compartments. For example, hydrophobic signal peptides are found at the amino terminus of proteins destined for the ER, while the sequence KFERQ (SEQ ID NO:29) (and other closely related sequences) is known to target intracellular polypeptides to lysosomes, while other sequences target polypeptides to endosomes.

One such trafficking sequence is the HLA-DRα leader sequence, Met Ala Ile Ser Gly Val Pro Val Leu Gly Phe Phe Ile Ile Ala Val Leu Met Ser Ala Gln Glu Ser Trp Ala (SEQ ID NO:18). The signal peptide may include only a portion (e.g., at least ten amino acid residues) of the specified 25 residue sequence, provided that portion is sufficient to cause trafficking of the polypeptide to the ER.

In some cases it is desirable to modify the portion of the peptide spanning the trafficking sequence and the sequence encoding the HPV E7 antigenic peptide to facilitate processing, i.e., cleavage, by the signal peptidase. Recognition sequences for signal peptides are described in Von Heijne, NAR 14:4683, 1986.

Standard techniques can be used to construct a DNA encoding the antigenic peptide (see, e.g., the techniques described in WO 94/04171). The construct may include additional sequences for enhancing expression in human cells, e.g., appropriate promoters, RNA stabilization sequences 5' and 3' to the coding sequence, introns (which can be placed at any location 5' or 3' within encoded sequence), and poly(A) addition sites, as well as an origin of replication and selectable markers enabling the constructs to replicate and be selected for in prokaryotic and/or eukaryotic hosts.

An example of a DNA sequence encoding an immunogenic HPV E7 antigen is the BIOTOPE$_{HPV}$ construct (SEQ ID NO:7), which is shown schematically in FIG. 1. This plasmid contains a minigene (SEQ ID NO: 5) at positions 3290–3413. The minigene encodes the HLA-DRα trafficking peptide linked to 12 residues of the A2.1/4 peptide. In the peptide encoded by the minigene, an alanine has been substituted for the amino terminal leucine in the A2.1/4 peptide in order to facilitate cleaving of the trafficking peptide from the immunogenic peptide by a signal peptidase. The BIOTOPE$_{HPV}$ construct also carries the immediate early promoter of human cytomegalovirus (CMV) at positions 2619–3315, and RNA stabilization sequences (RST) derived from the *Xenopus laevis* β-globin gene flanking the minigene (positions 3219–3279 and 3426–3624). To maximize export from the nucleus, the pre-mRNA expressed from the plasmid contains a chimeric intron between the coding sequence of the minigene and the SV40 polyadenylation site. The intron can also function if located between the promoter and the coding region.

Once in the cytoplasm of the cell, the mRNA transcribed from the minigene is translated to produce a 40 amino acid hybrid peptide. The first two amino acids are methionine and aspartic acid (derived from vector sequences), and the next 38 amino acids correspond to Met Ala Ile Ser Gly Val Pro Val Leu Gly Phe Phe Ile Ile Ala Val Leu Met Ser Ala Gln Glu Ser Trp Ala Ala Leu Met Gly Thr Leu Gly Ile Val Cys Pro Ile Cys (SEQ ID NO:6). The amino-terminal 25 amino acids of the 38-residue portion are identical in sequence to the non-polymorphic HLA-DRα chain gene leader sequence (SEQ ID NO:18). The last 13 amino acids have the sequence Ala Leu Met Gly Thr Leu Gly Ile Val Cys Pro Ile Cys (SEQ ID NO:4), which is the A2.1/4 peptide described above, but with an alanine residue substituted for the amino terminal leucine residue.

Also within the plasmid is a kanamycin resistance gene (positions 519–1313), which is driven by the SV40 early promoter (positions 131–484) and which has a thymidine kinase (TK) polyadenylation site (positions 1314–1758). The kanamycin resistance gene and accompanying regulatory sequences are for selection purposes only and can be removed from the plasmid if selection is not required or desired.

Once expressed in a cell, the encoded peptide can be processed into one of several HLA MHC class I binding epitopes. At least some of these are included in Table 1. These peptides can bind the HLA-A2 allele and may also bind other alleles, such as HLA-A1, HLA-A3, HLA-A11, HLA-A24. The MHC molecule, upon binding to the peptide, can activate a T cell response. MHC class II binding peptides may also be generated from the encoded peptide. These peptides would be expected to activate T helper cells or CTL upon presentation by the MHC class II expressing cells. Other receptors may also bind the encoded peptide or its processed fragments to activate immune cells such as NK or B cells. These cells may also be activated by cytokines elicited in response to the peptides of the invention.

The peptides and nucleic acids of the invention can be used as vaccines prophylactically or therapeutically in subjects known to be infected by HPV, suspected of being infected by HPV, or likely to become infected by HPV. Other suitable subjects include those displaying symptoms of, or likely to develop, HPV-associated conditions. The immunogenic peptides, and nucleic acids encoding these peptides, can be used as vaccines in preventing or treating conditions associated with infections of HPV strain 16, e.g., bowenoid papulosis, anal dysplasia, respiratory or conjunctival papillomas, cervical dysplasia, cervical cancer, vulval cancer, or prostate cancer. They can also be used to treat conditions associated with other HPV strains, especially those associated with HPV strains 18, 45, 6, 11, 35 and 31, which have regions of homology to the peptide of SEQ ID NO:3. These conditions include, e.g., exophytic condyloma (HPV strains 6 and 11), flat condyloma, especially of the cervix (HPV strains 6, 11, 16, 18, and 31), giant condyloma (HPV strains 6 and 11), cervical cancer (HPV strains 18, 31, and 33, in addition to HPV strain 16), respiratory and conjunctival papillomas (HPV 6 and 11), and infection with genital-tract HPVs (HPV 6, 11, and 16).

The immunogenic peptides or nucleic acids encoding the peptides can administered alone or in combination with other therapies known in the art, e.g., chemotherapeutic regimens, radiation, and surgery, to treat HPV infections, or diseases associated with HPV infections. In addition, the peptides and nucleic acids of the invention can be administered in combination with other treatments designed to enhance immune responses, e.g., by co-administration with adjuvants or cytokines (or nucleic acids encoding cytokines) as is well known in the art.

The peptides or nucleic acids of the invention can also be used in manufacture of a medicament for the prevention or treatment of HPV infection, or conditions associated with HPV infection.

Delivery of Immunogenic Peptides and Nucleic Acids Encoding Immunogenic Peptides The delivery systems of the invention may be used to deliver, into appropriate cells, peptides, or DNA constructs which express peptides, intended to stimulate an immune response against HPV. An advantage of DNA delivery is that the antigenic peptide is produced inside the target cell itself, where the interaction with a class I or class II MHC molecule to which the immunogenic peptide binds is kinetically favored. This is in contrast to standard vaccine protocols which do not specifically direct antigenic peptides to MHC molecules. In addition, the immune response directly stimulated by DNA vaccines of the invention is likely to be limited to a T cell mediated response, in contrast to standard vaccine protocols which result in a more generalized immune response, although it is possible that an antibody response may be indirectly induced when cells bearing viral particles are killed, or by other mechanisms.

The immunogenic peptides, or nucleic acids encoding the peptides, can be administered using standard methods, e.g., those described in Donnelly et al., J. Imm. Methods 176:145, 1994, and Vitiello et al., J. Clin. Invest. 95:341, 1995. Peptides and nucleic acids of the invention can be injected into subjects in any manner known in the art, e.g., intramuscularly, intravenously, intraarterially, intradermally, intraperitoneally, intranasally, intravaginally, intrarectally or subcutaneously, or they can be introduced into the gastrointestinal tract, the mucosa, or the respiratory tract, e.g., by inhalation of a solution or powder containing the microparticles. Administration can be local (e.g., at the cervix or other site of infection) or systemic.

The immunogenic peptides and nucleic acids encoding immunogenic peptides can be delivered in a pharmaceutically acceptable carrier such as saline, lipids, liposomes, microspheres, nanospheres, as colloidal suspensions, or as powders. They can be naked or associated or complexed with delivery vehicles and delivered using delivery systems known in the art, such as lipids, liposomes, microparticles, gold, nanoparticles, polymers, condensing agents, polysaccharides, polyamino acids, dendrimers, saponins, adsorption enhancing materials, or fatty acids.

It is expected that a dosage of approximately 0.1 to 100 $\mu$moles of the polypeptide, or of about 1 to 200 $\mu$g of DNA, would be administered per kg of body weight per dose. Where the patient is an adult human, vaccination regimens can include, e.g., intramuscular, intravenous, oral, or subcutaneous administrations of 10–1000 $\mu$g of pBIOTOPE$_{HPV}$ DNA when delivered in a microparticle, or of about 100–1000 $\mu$g of naked pBIOTOPE$_{HPV}$ DNA delivered intramuscularly or intradermally, repeated 3–6 times. Of course, as is well known in the medical arts, dosage for any given patient depends upon many factors, including the patient's size, body surface area, age, the particular compound to be administered, sex, time and route of administration, general health, and other drugs being administered concurrently. Determination of optimal dosage is well within the abilities of a pharmacologist of ordinary skill.

Other standard delivery methods, e,g, biolistic transfer, or ex vivo treatment, can also be used. In ex vivo treatment, e.g., antigen presenting cells (APCs), dendritic cells, peripheral blood mononuclear cells, or bone marrow cells, can be obtained from a patient or an appropriate donor and activated ex vivo with the immunogenic compositions, and then returned to the patient.

Microparticle Delivery of Synthetic Immunogenic Peptides or Plasmids Encoding Immunogenic Peptides Microparticles, including those described in U.S. Pat. No. 5,783,567, can be used as vehicles for delivering macromolecules such as DNA, RNA, or polypeptides into cells. They contain macromolecules embedded in a polymeric matrix or enclosed in a shell of polymer. Microparticles act to maintain the integrity of the macromolecule e.g., by maintaining enclosed DNA in a nondegraded state. Microparticles can also be used for pulsed delivery of the macromolecule, and for delivery at a specific site or to a specific cell or target cell population.

The polymeric matrix can be a biodegradable copolymer such as poly-lactic-co-glycolic acid, starch, gelatin, or chitin. Microparticles can be used in particular to maximize delivery of DNA molecules into a subject's phagocytotic cells. Alternatively, the microparticles can be injected or implanted in a tissue, where they form a deposit. As the deposit breaks down, the nucleic acid is released gradually over time and taken up by neighboring cells (including APCs) as free DNA.

Liposomal Delivery of Synthetic Immunogenic Peptides or Plasmids Encoding Immunogenic Peptides The immunogenic peptides of the invention can be administered into subjects via lipids, dendrimers, or liposomes using techniques that are well known in the art. For example, liposomes carrying immunogenic polypeptides or nucleic acids encoding immunogenic peptides are known to elicit CTL responses in vivo (Reddy et al., J. Immunol. 148:1585, 1992; Collins et al., J. Immunol. 148:3336–3341, 1992; Fries et al., Proc. Natl. Acad. Sci. USA 89:358, 1992; Nabel et al., Proc. Nat. Acad. Sci. (USA) 89:5157, 1992).

Delivery of Synthetic Immunogenic Peptides or Plasmids Encoding Immunogenic Peptides Using Saponin The peptides and nucleic acids of the invention can be administered by using Immune Stimulating Complexes (ISCOMS), which are negatively charged cage-like structures of 30–40 nm in size formed spontaneously on mixing cholesterol and Quil A (saponin), or saponin alone. The peptides and nucleic acids of the invention can be co-administered with the ISCOMS, or can be administered separately.

Protective immunity has been generated in a variety of experimental models of infection, including toxoplasmosis and Epstein-Barr virus-induced tumors, using ISCOMS as the delivery vehicle for antigens (Mowat et al., Immunology Today 12:383–385, 1991). Doses of antigen as low as 1 $\mu$g encapsulated in ISCOMS have been found to produce class I mediated CTL responses, where either purified intact HIV-1-IIIB gp 160 envelope glycoprotein or influenza hemagglutinin is the antigen (Takahashi et al., Nature 344:873–875, 1990).

Measuring Responses of the Immune System and of HPV Virus Infections to the Immunogenic Peptides or Nucleic Acids Encoding the Immunogenic Peptides The ability of immunogenic peptides, or nucleic acids encoding the same, to elicit an immune response can be assayed by using methods for measuring immune responses that are well known in the art. For example, the generation of cytotoxic T cells can be demonstrated in a standard $^{51}$Cr release assay, by measuring intracellular cytokine expression, or by using MHC tetramers. Standard assays, such as ELISA or ELISPOT, can also be used to measure cytokine profiles attributable to T cell activation. T cell proliferation can also be measured using assays such as $^3$H-thymidine uptake and other assays known in the art. B cell responses can be measured using art recognized assays such as ELISA.

Other methodologies, e.g., digital imaging, cytologic, colposcopic and histological evaluations, can also be used to evaluate the effects of immunogenic peptides, and of nucleic acids encoding the immunogenic peptides, on papilloma virus-associated lesions, or on papilloma virus levels generally.

The following are examples of the practice of the invention. They are not to be construed as limiting the scope of the invention in any way.

EXAMPLES

As described in the Examples below, experimental models were chosen to demonstrate the generation of vigorous CTL responses to plasmids encoding the immunogenic peptides of the invention, e.g., pBIOTOPE$_{HPV}$.

Initial screening of HPV peptide sequences was performed by assessing binding affinity to the human class I HLA-A2 molecule. This was done by measuring the changes in circular dichroism (CD) as the receptor/ligand complex "melted". Examples of this type of screening are shown in Example 1. of particular interest in Example 1 was the hybrid peptide A2.1/4, which contains at least two known epitopes.

Using a murine transgenic model, plasmids containing minigenes encoding these peptides were evaluated for their ability to generate HLA-A2 restricted CTLS (Examples 2 and 3). CTL activity, as measured using human target cells labeled with HPV peptides, was significantly increased over control targets for both the plasmids encoding A2.4 and A2.1/4, including the pA2.4 plasmid delivered in a PLGA microparticle.

Example 1

**Peptides Derived from HPV Strain 16 E7 Protein Bind Purified HLA-A*0201 with High Affinity**

To determine if peptides A2.1 (SEQ ID NO:1), A2.2 (SEQ ID NO:17), A2.4 (SEQ ID NO:2) A2.1/4 (SEQ ID NO:3), and A2.1/4 SQK bind with biological affinity to the human class I molecule HLA-A2 (for the peptides A2.1, A2.2, A2.4 and A2.1/4) or HLA-A3 (for the A2.1/4-SQK peptide), recombinant HLA-A2 or HLA-A3 was produced in *E. coli* and refolded in the presence of the HPV-derived peptides and purified human β$_2$-microglobulin. The resulting peptide-HLA complexes were then further purified by HPLC. To determine the precise thermokinetic interaction energy between receptor and ligand, each complex was "melted" while its structure was monitored by circular dichroism. The temperature required to "melt" the complex is an accurate indication of the affinity between receptor and ligand.

The results of the binding studies are shown in Table II.

TABLE II

Peptides binding HLA-A molecules

| NAME | Amino Acid Sequence | IC$_{50}$$^a$ | Tm♦ |
|---|---|---|---|
| A2.1 | SEQ ID NO: 1 | 8 | 47.8 |
| A2.2 | SEQ ID NO: 17 | 49 | 52.5 |
| A2.4 | SEQ ID NO: 2 | 153 | 41.5 |
| A2.1/4 | SEQ ID NO: 3 | ND | 41.0 |
| A2.1/4SQk | | ND | 47.8 |

$^a$IC$_{50}$ represents the amount (nM) of peptide required for 50% inhibition of binding of a radiolabeled standard peptide to HLA-A*0201 or HLA-A*0301 measured in a molecular binding assay.
♦Values represent the temperature in degrees Celsius at which 50% of the refolded complexes are melted. HLA-A2 and HLA-A3 will not refold in the absence of a peptide ligand of sufficient affinity.

Of particular interest is a hybrid peptide A2.1/4, which contains at least two known overlapping epitopes, A2.1 and A2.4, each of which is presented by HLA-A2 positive human cervical tumor cells expressing the HPV 16 E7 protein (Ressing et al., J. Immunology 154:5934, 1995). Of the peptides studied, A2.4 is predicted to be the most capable of eliciting cross reactive immune responses between HPV strains. Moreover, the hybrid peptide generates both the A2.1 and A2.4 peptides; administration of pBIOTOPE$_{HPV}$ to mice was found to generate T cell responses to both immunogenic peptides.

Example 2

Induction of HPV-Specific CTL in HLA-Transgenic Mice Immunized with Intramuscular Injections of a Plasmid Encoding the HPV Strain 16 Derived A2.4 Peptide

To demonstrate that a plasmid encoding the A2.4 peptide (SEQ ID NO:2) produced HPV peptides in vivo and that CTL to these peptides were generated, a transgenic animal model was employed. The HLA-A2/K$^b$ mouse line produces a hybrid MHC class I molecule. In this hybrid, the peptide binding domains (α1 and α2) are derived from the human class I molecule HLA-A*0201, whereas the domain (α3) which interacts with the CD8 co-receptor on CTLs is derived from the murine class I molecule K$^b$. The resulting animal is capable of responding to immunogens which contain HLA-A2 restricted epitopes and of generating murine CTLs that recognize human target cells expressing HLA-A2 (Vitiello et al., J. Exp. Med. 173:1007, 1991).

6–8 week old HLA-A2/K$^b$ females were immunized with either a plasmid encoding the A2.4 peptide having the amino terminal leucine replaced with an alanine residue, or with a null vector. Injections were performed with 50 μg of plasmid DNA injected as "naked DNA" (that is, with no liposome, microparticle, or other carrier) into each anterior tibialis muscle. A booster immunization was performed 14 days after the first immunization, and a second booster immunization was performed 14 days after the first boost. Ten days following the third immunization, splenocytes were harvested and stimulated in vitro with syngeneic lipopolysaccharide (LPS) blasts which had been incubated with the synthetic A2.4 peptide. After 4 days of co-culture, CTL activity was measured on human targets labeled with HPV peptides (Table III).

TABLE III

Lysis of Human Cells Labeled with HPV-derived Peptides by Murine CTL from HLA-Transgenic Mice Immunized with Plasmid Encoding an A2.4 peptide.

| IMMUNOGEN | % LYSIS OF TARGET CELLS* |
|---|---|
| pVA2.4 | 28.7 ± 0.7* |
| Vector | 6.8 ± 2.9* |

*Data are reported as the mean lysis values at 100:1 effector to target ratio. Error is reported as the standard deviation; p = 0.05 by Students t-test.

Mice immunized with a plasmid encoding the A2.4 peptide generate CTL that lyse human targets expressing HLA-A2 and the appropriate HPV peptide. This response is significantly greater than that achieved by immunization with null vector DNA alone.

Example 3

Plasmid DNA Encoding the A2.1/4 Peptide Delivered to Mice in PLGA Microparticles Elicits CTL Responses

6–8 week old HLA-A2/K$^b$ females were immunized intraperitoneally one time with 2–5 μg of PLGA microparticles containing plasmid pBIOTOPE$_{HPV}$. Seven days following the immunization, splenocytes were harvested and in vitro stimulated with IL-2. After 2 days, CTL activity was measured on human targets labeled with HPV peptides (HPV(+)), or lacking HPV peptide (HPV(−)), at an E:T ratio of 50:1 (Table IV).

TABLE IV

Lysis of Human Cells Labeled with HPV-
derived Peptides by Murine Splenocytes from HLA-
Transgenic Mice Immunized with PLGA Microparticles
Containing pBIOTOPE$_{HPV}$

| | % LYSIS OF TARGET CELLS | |
|---|---|---|
| IMMUNOGEN | HPV (+) | HPV (−) |
| pBIOTOPE$_{HPV}$ | 17.4 ± 2.8* | 3.9 ± 4.2* |

Data are reported as the mean lysis values from three individual measurements.
*Error is reported as the standard deviation; p value <0.05 as determined by the Students t-test.

Thus, mice immunized with PLGA microparticles containing pBIOTOPE$_{HPV}$ generate CTL that lyse human targets expressing HLA-A2 and A2.1/4 peptide.

Example 4

Synthetic Peptides Derived from HPV Type 16 Activate Human CTL

Peripheral blood mononuclear cells (PBMC) from an HLA-A2$^+$ donor were cultured in vitro for two rounds of stimulation in the presence of 300 units of IL-2 and peptide A2.1/4 (LLMGTLGIVCPIC) (SEQ ID NO:3) or an immunodominant peptide having the amino acid sequence GILGFVFTL (SEQ ID NO:24) from influenza virus, which was used as a positive control.

Seven days after the second stimulation, each culture was subdivided into two subgroups. One subgroup of each culture was stimulated for an additional 7 hours with the respective peptide ("the third peptide stimulation"), while the other subgroups were cultured without the peptide. All samples were pretreated with brefeldin A to prevent cytokine secretion. The cells were then subjected to triple color flow cytometry staining for CD8, CD16, and interferon-γ.

Figure 2:
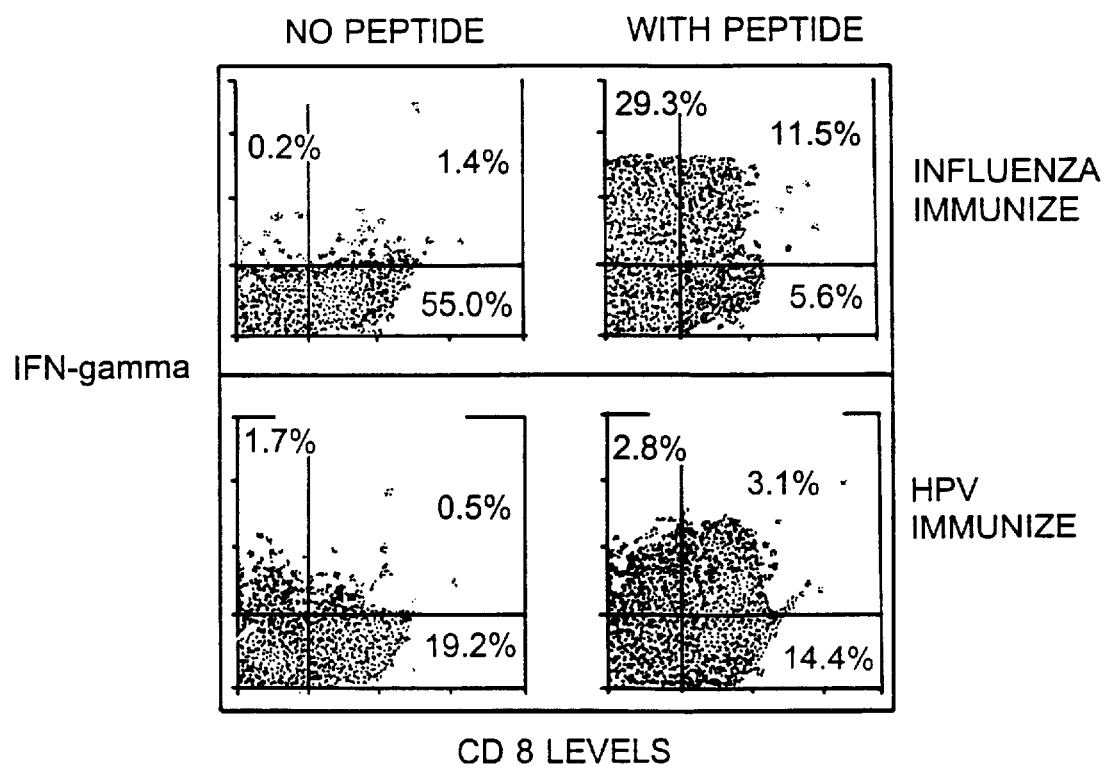
FIG. 2 is a graph showing the results of subjecting cells to triple color flow cytometry staining for CD8, CD16, and interferon-gamma.

The results of the experiments are shown in FIG. 2. For cells treated with the A2.1/4 peptide, 28% of the cells subjected to the third peptide stimulation stained positive for interferon-γ, compared to 1.7% of the cells that did not receive a final stimulation. The percentage of CD8$^+$ cells in cells receiving a third stimulation with peptide was 14.4%, while 19.2% of the cells which did not received a third stimulation were CD8$^+$. Overall, 3.1% of the PBMC receiving a final pulse of the A2.1/4 peptide were activated CTL, i.e., were CD8$^+$ CD16$^-$ IFN-γ$^+$, compared to 0.5% of the cells receiving no final pulse of HPV-derived peptide.

For cells treated with the influenza peptide, 11.5% of the cells receiving a third stimulation with the influenza peptide were positive for interferon γ, compared to 1.7% of the cells that did not receive a third stimulation. For cells cultured with influenza peptide, 11.5% of the cells given a final pulse of influenza peptide were activated, compared to 1.49% of cells which were not given a final pulse of influenza.

Figure 3:
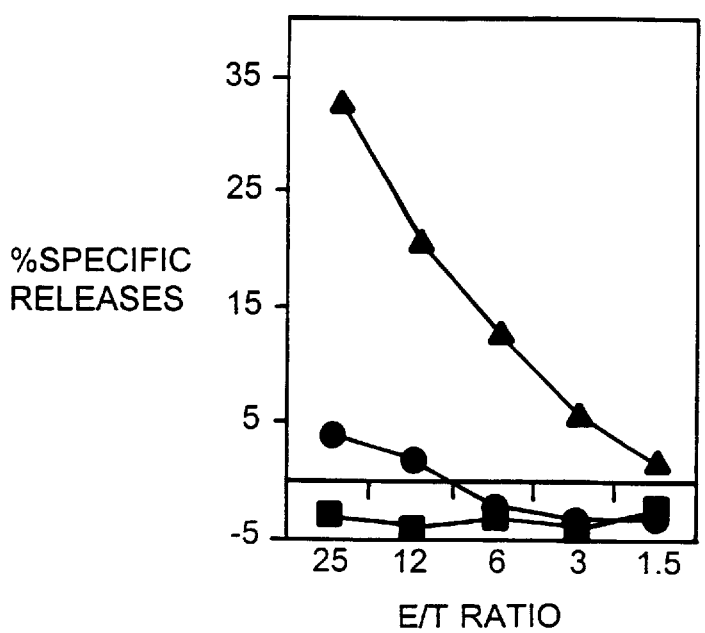
FIG. 3 is a graph showing CTL lysis of an HLA-A2$^+$, HPV16$^+$ cell line with T cells from an HLA-A2$^+$ donor stimulated with an influenza peptide (-■-), the A2.1 peptide (-●-), or the A2.4-C peptide (-▲-).
Figure 4:
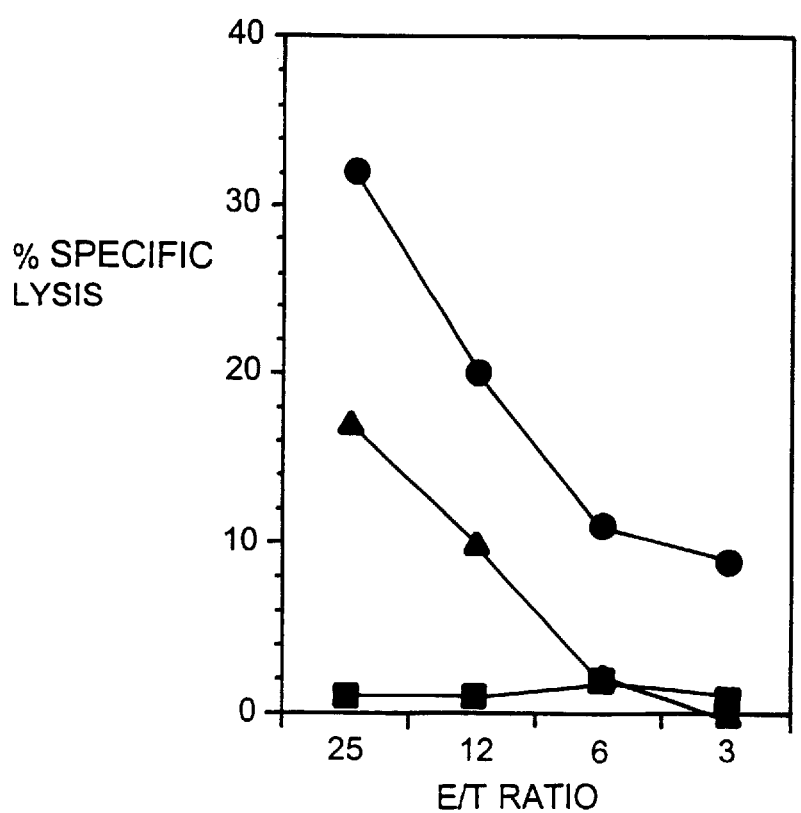
FIG. 4 is a graph showing CTL lysis of an HLA-A2$^+$, HPV16$^+$ cell line with T cells from a second HLA-A2$^+$ donor stimulated with an influenza peptide (-■-), the A2.1 peptide (-●-), or the A2.4 peptide (-▲-).

FIGS. 3 and 4 demonstrate that CTL specific for the A2.1 or A2.4-C peptides can recognize and lyse HPV 16-infected cells. FIG. 3 shows CTL-mediated lysis of an HLA-A2$^+$, HPV-16$^+$ transformed line (Caski) by T cell populations exposed to peptide A2.1, A2.4-C, or a peptide derived from influenza virus ("Flu"). Effector/target (E/T) ratios ranging from 25 to 1.5 were used. The peptide A2.4-C was highly effective at inducing lysis, with nearly 35% release detected at an E/T ratio of 25:1. The A2.1 peptide was less effective, but nevertheless caused much higher percentages of lysis at E/T ratios of 25:1 and 12:1 than did the influenza peptide.

Results with PBL isolated from a second HLA-A2$^+$ individual and subjected to two rounds of stimulation with peptide A2.1, peptide A2.4, or the influenza peptide ("Flu") are shown in FIG. 4. Both the A2.1 and A2.4 peptides induced higher levels of lysis than did the influenza peptide.

These observations demonstrate that the A2.1/4 peptide, or peptides derived therefrom, can activate and expand PBL from humans, and that these peptides can cause CTL-mediated lysis of target cells transformed with HPV16.

Other Embodiments

It is to be understood that while the invention has been described in conjunction with the detailed description thereof, that the foregoing description is intended to illustrate and not limit the scope of the appended claims. Other aspects, advantages; and modifications are within the scope of the following claims.

What is claimed is:

1. A polypeptide comprising a first peptide and a second peptide linked by a peptide bond, the first peptide being a peptide which controls intracellular trafficking of a peptide to which it is attached, and the second peptide consisting of a sequence 8–18 amino acids in length comprising the sequence Thr Leu Gly Ile Val Cys Pro Ile (SEQ ID NO:20).

2. The polypeptide of claim 1, wherein the sequence of the second peptide comprises the amino acid sequence Leu Met Gly Thr Leu Gly Ile Val Cys Pro Ile Cys (SEQ ID NO:16).

3. The polypeptide of claim 2, wherein the sequence of the first peptide comprises the amino acid sequence Met Ala Ile Ser Gly Val Pro Val Leu Gly Phe Phe Ile Ile Ala Val Leu Met Ser Ala Gln Glu Ser Trp Ala (SEQ ID NO:18).

4. The polypeptide of claim 2, wherein the amino acid sequence of the second peptide is Xaa Leu Met Gly Thr Leu Gly Ile Val Cys Pro Ile Cys, Xaa being Met, Leu, Ala, Ser, Arg, Lys, Gly, Gln, Asp, or Glu (SEQ ID NO:19).

5. The polypeptide of claim 2, wherein the amino acid sequence of the second polypeptide is Ala Leu Met Gly Thr Leu Gly Ile Val Cys Pro Ile Cys (SEQ ID NO:4).

6. The polypeptide of claim 3, wherein the amino acid sequence of the second peptide is Xaa Leu Met Gly Thr Leu Gly Ile Val Cys Pro Ile Cys, Xaa being Met, Leu, Ala, Ser, Arg, Lys, Gly, Gln, Asp, or Glu (SEQ ID NO:19).

7. The polypeptide of claim 3, wherein the amino acid sequence of the second peptide is Ala Leu Met Gly Thr Leu Gly Ile Val Cys Pro Ile Cys (SEQ ID NO:4).

8. A therapeutic composition comprising:
    (a) the polypeptide of claim 2; and
    (b) a pharmaceutically acceptable carrier.

9. A therapeutic composition comprising:
    (a) the polypeptide of claim 1; and
    (b) a pharmaceutically acceptable carrier.

10. A microparticle comprising a polymeric matrix and the polypeptide of claim 2.

11. A microparticle comprising a polymeric matrix and the polypeptide of claim 1.

12. A liposome or immune-stimulating complex (ISCOM) comprising the poiypeptide of claim 2.

13. A liposome or ISCOM comprising the polypeptide of claim 1.

14. A substantially pure peptide less than 19 amino acids in length, wherein the peptide comprises the amino acid sequence Leu Leu Met Gly Thr Leu Gly Ile Val Cys Pro Ile Cys (SEQ ID NO:3).

15. The peptide of claim 14, wherein the peptide's amino acid sequence comprises the amino acid sequence Leu Leu Met Gly Thr Leu Gly Ile Val Cys Pro Ile Cys Ser Gin Lys (SEQ ID NO:25).

16. The peptide of claim 14, wherein the peptide's amino acid sequence consists of the amino acid sequence Leu Leu Met Gly Thr Leu Gly Ile Val Cys Pro Tie Cys (SEQ ID NO:3), and optionally an amino terminal methionine.

17. A substantially pure peptide less than 19 amino acids in length, wherein the peptide comprises the amino acid sequence Xaa Leu Met Gly Thr Leu Gly Ile Val Cys Pro Ile Cys (SEQ ID NO:19), Xaa being Met, Ala, Ser, Arg, Lys, Gly, Gln, Asp, or Glu.

18. The peptide of claim 17, wherein the peptide's amino acid sequence comprises the amino acid sequence Ala Leu Met Gly Thr Leu Gly Ile Val Cys Pro Ile Cys (SEQ ID NO:4).

19. A substantially pure peptide consisting of an amino acid sequence selected from the group consisting of:

Met Ala Ile Ser Gly Val Pro Val Leu Gly Phe Phe Ile Ile Ala Val Leu Met Ser Ala Gln Glu Ser Trp Ala Ala Leu Met Gly Thr Leu Gly Ile Val Cys Pro Ile Cys (SEQ ID NO:6);

Leu Met Gly Thr Leu Gly Ile Val Cys Pro Ile Cys (SEQ ID NO:16); and

Met Gly Thr Leu Gly Ile Val Cys Pro Ile Cys Ser Gin Lys (SEQ ID NO:32), wherein the peptide optionally includes an amino terminal methionine.

20. A therapeutic composition comprising:
(a) the peptide of claim 14; and
(b) a pharmaceutically acceptable carrier.

21. A therapeutic composition comprising:
(a) the peptide of claim 17; and
(b) a pharmaceutically acceptable carrier.

22. A therapeutic composition comprising:
(a) the peptide of claim 19; and
(b) a pharmaceutically acceptable carrier.

23. A microparticle comprising a polymeric matrix and the peptide of claim 14.

24. A microparticle comprising a polymeric matrix and the peptide of claim 17.

25. A microparticle comprising a polymeric matrix and the peptide of claim 19.

26. A liposome or ISCOM comprising the peptide of claim 14.

27. A liposome or ISCOM comprising the peptide of claim 17.

28. A liposome or ISCOM comprising the peptide of claim 19.

* * * * *